(12) United States Patent
Cho et al.

(10) Patent No.: US 9,434,751 B2
(45) Date of Patent: Sep. 6, 2016

(54) ALKYLALKOXYSILANE COMPOUNDS CONTAINING ETHER GROUP AND DIALKYLAMINO GROUP AND PROCESS FOR PREPARING THE COMPOUNDS

(71) Applicant: KOREA KUMHO PETROCHEMICAL CO., LTD., Seoul (KR)

(72) Inventors: Hanjoung Cho, Daejeon (KR); Jae Young Ko, Daejeon (KR); Dae Hyung Lee, Daejeon (KR); Cheol Min Park, Gwangju (KR); Sang Chul Ji, Incheon (KR)

(73) Assignee: KOREA KUMHO PETROCHEMICAL CO., LTD., Seoul (KR)

( * ) Notice: Subject to any disclaimer, the term of this patent is extended or adjusted under 35 U.S.C. 154(b) by 156 days.

(21) Appl. No.: 14/012,046

(22) Filed: Aug. 28, 2013

(65) Prior Publication Data

US 2014/0088320 A1    Mar. 27, 2014

(30) Foreign Application Priority Data

Sep. 24, 2012 (KR) ........................ 10-2012-0105776

(51) Int. Cl.
*C07F 7/18* (2006.01)

(52) U.S. Cl.
CPC ............. *C07F 7/1876* (2013.01); *C07F 7/184* (2013.01); *C07F 7/1836* (2013.01); *C07F 7/1852* (2013.01)

(58) Field of Classification Search
CPC .... C07F 7/1876; C07F 7/1836; C07F 7/184; C07F 7/1852
See application file for complete search history.

(56) References Cited

U.S. PATENT DOCUMENTS 8,106,130 B2  1/2012  Fukuoka et al.
2010/0152369 A1  6/2010  Shibata et al.

*Primary Examiner* — Paul A Zucker
*Assistant Examiner* — Mark Luderer
(74) *Attorney, Agent, or Firm* — Hauptman Ham, LLP

(57) ABSTRACT

The present invention relates to an alkylalkoxysilane compound of a novel structure which has an ether group and an dialkylamino group in an alkyl chain of the alkylalkoxysilane and thus has remarkably improved storage stability and hydrophilicity and a method for preparing same.

3 Claims, No Drawings

ALKYLALKOXYSILANE COMPOUNDS CONTAINING ETHER GROUP AND DIALKYLAMINO GROUP AND PROCESS FOR PREPARING THE COMPOUNDS

CROSS-REFERENCE TO RELATED APPLICATIONS

This application claims priority under 35 U.S.C. §119 to Korean Patent Application No. 10-2012-0105776, filed on Sep. 24, 2012, in the Korean Intellectual Property Office, the disclosure of which is incorporated herein by reference in its entirety.

BACKGROUND (a) Technical Field

The present invention relates to an alkylalkoxysilane compound of a novel structure having an ether group and a dialkylamino group in an alkyl chain of the alkylalkoxysilane and a method for preparing same.

(b) Background Art

Owing to specific reactivity different from that of general hydrocarbon compounds, organosilane compounds are widely used in various fields. For example, chlorosilane compounds are used as a silylating agent or as a packing material in liquid chromatography. Alkoxysilane compounds are used as a penetrable waterproofing agent and alkoxysilane compounds having amine functional groups are used as a coupling agent or a polymer end modifier.

U.S. Pat. No. 8,106,130 discloses use of an alkylalkoxysilane compound having at least two tertiary amine groups in the carbon chain as a polymer end modifier and US Patent Application Publication No. 2010/0152369 discloses use of an alkylalkoxysilane compound having an N,N-bis(trialkylsilyl)amino group as a polymer end modifier. However, when the alkylalkoxysilane compounds developed thus far are used as a polymer end modifier, mechanical properties or dynamic viscoelastic properties are relatively unsatisfactory. It is because the hydrophobicity conferred by the nitrogen atom of the amine group after the end modification is insufficient.

The inventors of the present invention have made efforts to synthesize a novel alkylalkoxysilane compound that can be used widely as a polymer end modifier, a coupling agent, etc. As a result, they have found out that, by using a polymer end modifier further having an oxygen heteroatom having high electronegativity and capable of inducing interaction with silica adjacent to the nitrogen heteroatom of a dialkylamine group, the mechanical properties or dynamic viscoelastic properties of the end-modified polymer can be effectively improved.

SUMMARY

The present invention is directed to providing an alkylalkoxysilane compound having an ether group and a dialkylamino group in an alkyl chain.

The present invention is also directed to providing a method for preparing an alkylalkoxysilane compound.

In an aspect, the present invention provides an alkylalkoxysilane compound represented by Chemical Formula 1:

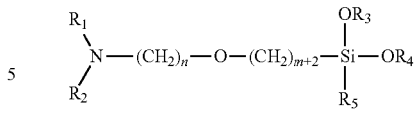

[Chemical Formula 1]

wherein $R_1$, $R_2$, $R_3$ and $R_4$ represent the same or different unsubstituted $C_1$-$C_{10}$ alkyl group; $R_5$ represents an unsubstituted $C_1$-$C_{10}$ alkyl group or an unsubstituted $C_1$-$C_{10}$ alkoxy group; n represents an integer from 0 to 5; and m represents an integer from 0 to 3.

Other features and aspects of the present invention will be apparent from the following detailed description, drawings and claims.

DETAILED DESCRIPTION

Hereinafter, reference will now be made in detail to various embodiments of the present invention, examples of which are illustrated in the accompanying drawings and described below. While the invention will be described in conjunction with exemplary embodiments, it will be understood that the present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

The present invention provides a novel alkylalkoxysilane compound represented by Chemical Formula 1:

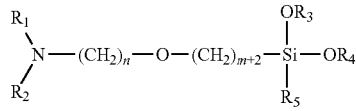

[Chemical Formula 1]

wherein $R_1$, $R_2$, $R_3$ and $R_4$ represent the same or different unsubstituted $C_1$-$C_{10}$ alkyl group; $R_5$ represents an unsubstituted $C_1$-$C_{10}$ alkyl group or an unsubstituted $C_1$-$C_{10}$ alkoxy group; n represents an integer from 0 to 5; and m represents an integer from 0 to 3.

Since the alkylalkoxysilane compound represented by Chemical Formula 1 according to the present invention has two or more alkoxy groups, it can chemically bind to commercially available silica. Since the alkoxy group has a tertiary amine group and an ether group, the alkylalkoxysilane compound can more closely access to an organic or inorganic material through hydrogen bonding or van der Waals interaction. Owing to such characteristics, the alkylalkoxysilane compound represented by Chemical Formula 1 has improved compatibility with an organic polymer or an inorganic material such as silica and has improved mechanical strength, processability, etc. due to increased dispersibility.

Specifically, in the alkylalkoxysilane compound represented by Chemical Formula 1 according to the present invention, $R_1$, $R_2$, $R_3$, and $R_4$ may respectively represent methyl, ethyl, n-propyl, isopropyl, n-butyl, s-butyl or t-butyl, $R_5$ may represent methyl, ethyl, n-propyl, isopropyl, n-butyl, s-butyl, t-butyl, methoxy, ethoxy, n-propoxy, isopropoxy, n-butoxy, s-butoxy or t-butoxy n represents an integer from 0 to 5 and m represents an integer from 0 to 3.

Specific examples of the alkylalkoxysilane compound represented by Chemical Formula 1 according to the present invention may include:

N,N-dimethyl-1-(2-(trimethoxysilyl)ethoxy)methanamine,
N,N-dimethyl-1-(2-(dimethoxymethylsilyl)ethoxy)methanamine,
N,N-dimethyl-1-(2-(dimethoxyethylsilyl)ethoxy)methanamine,
N,N-dimethyl-1-(2-(triethoxysilyl)ethoxy)methanamine,
N,N-dimethyl-1-(2-(diethoxymethylsilyl)ethoxy)methanamine,
N,N-dimethyl-1-(2-(diethoxyethylsilyl)ethoxy)methanamine,
N,N-diethyl-1-(2-(trimethoxysilyl)ethoxy)methanamine,
N,N-diethyl-1-(2-(dimethoxymethylsilyl)ethoxy)methanamine,
N,N-diethyl-1-(2-(dimethoxyethylsilyl)ethoxy)methanamine,
N,N-diethyl-1-(2-(triethoxysilyl)ethoxy)methanamine,
N,N-diethyl-1-(2-(diethoxymethylsilyl)ethoxy)methanamine,
N,N-diethyl-1-(2-(diethoxyethylsilyl)ethoxy)methanamine,
N,N-dimethyl-1-(3-(trimethoxysilyl)propoxy)methanamine,
N,N-dimethyl-1-(3-(dimethoxymethylsilyl)propoxy)methanamine,
N,N-dimethyl-1-(3-(dimethoxyethylsilyl)propoxy)methanamine,
N,N-dimethyl-1-(3-(triethoxysilyl)propoxy)methanamine,
N,N-dimethyl-1-(3-(diethoxymethylsilyl)propoxy)methanamine,
N,N-dimethyl-1-(3-(diethoxyethylsilyl)propoxy)methanamine,
N,N-diethyl-1-(3-(trimethoxysilyl)propoxy)methanamine,
N,N-diethyl-1-(3-(dimethoxymethylsilyl)propoxy)methanamine,
N,N-diethyl-1-(3-(dimethoxyethylsilyl)propoxy)methanamine,
N,N-diethyl-1-(3-(triethoxysilyl)propoxy)methanamine,
N,N-diethyl-1-(3-(diethoxymethylsilyl)propoxy)methanamine,
N,N-diethyl-1-(3-(diethoxyethylsilyl)propoxy)methanamine,
N,N-dimethyl-2-(2-(trimethoxysilyl)ethoxy)ethanamine,
N,N-dimethyl-2-(2-(dimethoxymethylsilyl)ethoxy)ethanamine,
N,N-dimethyl-2-(2-(dimethoxyethylsilyl)ethoxy)ethanamine,
N,N-dimethyl-2-(2-(triethoxysilyl)ethoxy)ethanamine,
N,N-dimethyl-2-(2-(diethoxymethylsilyl)ethoxy)ethanamine,
N,N-dimethyl-2-(2-(diethoxyethylsilyl)ethoxy)ethanamine,
N,N-diethyl-2-(2-(trimethoxysilyl)ethoxy)ethanamine,
N,N-diethyl-2-(2-(dimethoxymethylsilyl)ethoxy)ethanamine,
N,N-diethyl-2-(2-(dimethoxyethylsilyl)ethoxy)ethanamine,
N,N-diethyl-2-(2-(triethoxysilyl)ethoxy)ethanamine,
N,N-diethyl-2-(2-(diethoxymethylsilyl)ethoxy)ethanamine,
N,N-diethyl-2-(2-(diethoxyethylsilyl)ethoxy)ethanamine,
N,N-dimethyl-2-(3-(trimethoxysilyl)propoxy)ethanamine,
N,N-dimethyl-2-(3-(dimethoxymethylsilyl)propoxy)ethanamine,
N,N-dimethyl-2-(3-(dimethoxyethylsilyl)propoxy)ethanamine,
N,N-dimethyl-2-(3-(triethoxysilyl)propoxy)ethanamine,
N,N-dimethyl-2-(3-(diethoxymethylsilyl)propoxy)ethanamine,
N,N-dimethyl-2-(3-(diethoxyethylsilyl)propoxy)ethanamine,
N,N-diethyl-2-(3-(trimethoxysilyl)propoxy)ethanamine,
N,N-diethyl-2-(3-(dimethoxymethylsilyl)propoxy)ethanamine,
N,N-diethyl-2-(3-(dimethoxyethylsilyl)propoxy)ethanamine,
N,N-diethyl-2-(3-(triethoxysilyl)propoxy)ethanamine,
N,N-diethyl-2-(3-(diethoxymethylsilyl)propoxy)ethanamine,
N,N-diethyl-2-(3-(diethoxyethylsilyl)propoxy)ethanamine,
N,N-dimethyl-3-(2-(trimethoxysilyl)ethoxy)propan-1-amine,
N,N-dimethyl-3-(2-(dimethoxymethylsilyl)ethoxy)propan-1-amine,
N,N-dimethyl-3-(2-(dimethoxyethylsilyl)ethoxy)propan-1-amine,
N,N-dimethyl-3-(2-(triethoxysilyl)ethoxy)propan-1-amine,
N,N-dimethyl-3-(2-(diethoxymethylsilyl)ethoxy)propan-1-amine,
N,N-dimethyl-3-(2-(diethoxyethylsilyl)ethoxy)propan-1-amine,
N,N-diethyl-3-(2-(trimethoxysilyl)ethoxy)propan-1-amine,
N,N-diethyl-3-(2-(dimethoxymethylsilyl)ethoxy)propan-1-amine,
N,N-diethyl-3-(2-(dimethoxyethylsilyl)ethoxy)propan-1-amine,
N,N-diethyl-3-(2-(triethoxysilyl)ethoxy)propan-1-amine,
N,N-diethyl-3-(2-(diethoxymethylsilyl)ethoxy)propan-1-amine,
N,N-diethyl-3-(2-(diethoxyethylsilyl)ethoxy)propan-1-amine,
N,N-dimethyl-3-(3-(trimethoxysilyl)propoxy)propan-1-amine,
N,N-dimethyl-3-(3-(dimethoxymethylsilyl)propoxy)propan-1-amine,
N,N-dimethyl-3-(3-(dimethoxyethylsilyl)propoxy)propan-1-amine,
N,N-dimethyl-3-(3-(triethoxysilyl)propoxy)propan-1-amine,
N,N-dimethyl-3-(3-(diethoxymethylsilyl)propoxy)propan-1-amine,
N,N-dimethyl-3-(3-(diethoxyethylsilyl)propoxy)propan-1-amine,
N,N-diethyl-3-(3-(trimethoxysilyl)propoxy)propan-1-amine,
N,N-diethyl-3-(3-(dimethoxymethylsilyl)propoxy)propan-1-amine,
N,N-diethyl-3-(3-(dimethoxyethylsilyl)propoxy)propan-1-amine,
N,N-diethyl-3-(3-(triethoxysilyl)propoxy)propan-1-amine,
N,N-diethyl-3-(3-(diethoxymethylsilyl)propoxy)propan-1-amine and
N,N-diethyl-3-(3-(diethoxyethylsilyl)propoxy)propan-1-amine.

The present invention also provides a method for preparing the alkylalkoxysilane compound represented by Chemical Formula 1.

The preparation method according to the present invention includes, as described in Scheme 1, preparing an intermediate compound represented by Chemical Formula 4 by coupling an allyl halide compound represented by Chemical Formula 2 with an N,N-dialkylaminoalkanol represented by Chemical Formula 3 in the presence of a base; and preparing an alkylalkoxysilane compound represented by Chemical Formula 1 by hydrosilylating the intermediate compound represented by Chemical Formula 4 with a silane compound represented by Chemical Formula 5.

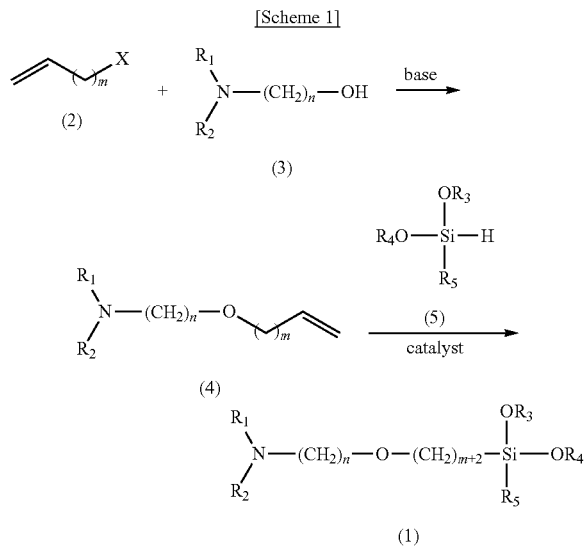

In Scheme 1, $R_1$, $R_2$, $R_3$, $R_4$, $R_5$, m and n are the same as defined above.

The first step of the preparation method according to Scheme 1 is conducted at −30° C. to 40° C. in the presence of a base. The base may be hydride, hydroxide, carbonate, bicarbonate, etc. of an alkali metal or an alkaline earth m metal. Specifically, sodium hydride (NaH) or sodium hydroxide (NaOH) may be used. The selection of a reaction solvent in the first step is not particularly limited. Any inert solvent not affecting the reaction may be used. Specifically, the reaction solvent may be a polar solvent such as dimethyl formaldehyde when considering the solubility of reactants.

The second step (hydrosilylation) of the preparation method according to Scheme 1 is conducted in the presence of a platinum (Pt) catalyst. The hydrosilylation reaction may be conducted under heating to improve reaction rate and reaction yield. Specifically, the reaction may be conducted under reflux. The reflux temperature may be approximately 100° C. to 180° C. although it may vary depending on the solvent used. The selection of a reaction solvent in the second step is not particularly limited either. Any inert solvent not affecting the reaction may be used. Specifically, the reaction solvent may be an aromatic solvent such as benzene and toluene.

Since the alkylalkoxysilane compound represented by Chemical Formula 1 according to the present invention has a tertiary amine group and an ether group in one molecule, it is useful as a modifier that confers hydrophilicity to an organic or inorganic material. Further, the alkylalkoxysilane compound represented by Chemical Formula 1 according to the present invention has superior long-term storage stability at room temperature.

EXAMPLES

The present invention will be described in more detail through examples.

The following examples are for illustrative purposes only and it will be apparent to those skilled in the art not that the scope of this invention is not limited by the examples.

Examples

Example 1

N,N-dimethyl-2-(3-(trimethoxysilyl)propoxy)ethanamine

Sodium hydride (17.5 g) and dimethyl formaldehyde (400 mL) were added to a 2-L round-bottom flask. After cooling the flask to 0° C. by immersing in an ice bath, 2-dimethylaminoethanol (0.398 mol) was added. After stirring for about 30 minutes and adding allyl bromide (0.4378 mol), the mixture was stirred for 3 hours after raising the temperature of the reactor to room temperature. Upon completion of reaction, the reaction was terminated by adding water to the flask and the product was extracted using diethyl ether. The extract was concentrated under reduced pressure and used in the next step without further purification. After filtration under reduced pressure, 2-(allyloxy)-N,N-dimethylethanamine was obtained through fractional distillation. Structural analysis was performed by nuclear magnetic resonance (NMR) spectroscopy.

$^1$H NMR (400 MHz, CDCl$_3$) δ 5.90 (1H, m), 5.24 (1H, d, J=17.2 Hz), 5.15 (1H, d, J=17.2 Hz), 3.97 (2H, d, J=6.0 Hz), 3.50 (2H, t, J=6.0 Hz), 2.49 (2H, t, J=5.6 Hz), 2.24 (6H, s); $^{13}$C NMR (100 MHz, CDCl$_3$) δ 134.9, 117.1, 72.1, 68.1, 58.9, 45.9.

After adding toluene (200 mL) to a round-bottom flask containing 2-(allyloxy)-N,N-dimethylethanamine (0.398 mol) and dissolving trimethoxysilane (0.398 mol), a commercially available platinum(0)-1,3-divinyl-1,1,3,3-tetramethyldisiloxane solution was added and the mixture was stirred for 24 hours under reflux. Upon completion of reaction, after removing the solvent through distillation under reduced pressure, 0.342 mol (yield: 86%) of the target compound was obtained by extracting with water and diethyl ether. $^1$H and $^{13}$C NMR spectroscopic data of the purified N,N-dimethyl-2-(3-(trimethoxymethylsilyl) propoxy)ethanamine are as follows.

$^1$H NMR (400 MHz, CDCl$_3$) δ 3.52 (9H, s), 3.49 (2H, t, J=6.4 Hz), 3.38 (2H, J=6.4 Hz), 2.47 (2H, t, J=6.4 Hz), 2.24 (6H, s), 1.67 (2H, m), 0.64 (2H, t, J=8 Hz); $^{13}$C NMR (100 MHz, CDCl$_3$) δ 73.3, 68.8, 58.9, 50.5, 45.9, 22.7, 5.3.

Example 2

N,N-dimethyl-2-(3-(dimethoxymethylsilyl)propoxy) ethanamine

Sodium hydride (17.5 g) and dimethyl formaldehyde (400 mL) were added to a 2-L round-bottom flask. After cooling the flask to 0° C. by immersing in an ice bath, 2-dimethylaminoethanol (0.398 mol) was added. After stirring for about 30 minutes and adding allyl bromide (0.4378 mol), the mixture was stirred for 3 hours after raising the temperature of the reactor to room temperature. Upon completion of reaction, the reaction was terminated by adding water to the flask and the product was extracted using diethyl ether. The extract was concentrated under reduced pressure and used in the next step without further purification. After filtration under reduced pressure, 2-(allyloxy)-N,N-dimethylethanamine was obtained through fractional distillation. Structural analysis was performed by NMR spectroscopy.

$^1$H NMR (400 MHz, CDCl$_3$) δ 5.90 (1H, m), 5.24 (1H, d, J=17.2 Hz), 5.15 (1H, d, J=17.2 Hz), 3.97 (2H, d, J=6.0 Hz), 3.50 (2H, t, J=6.0 Hz), 2.49 (2H, t, J=5.6 Hz), 2.24 (6H, s); $^{13}$C NMR (100 MHz, CDCl$_3$) δ 134.9, 117.1, 72.1, 68.1, 58.9, 45.9.

After adding toluene (200 mL) to a round-bottom flask containing 2-(allyloxy)-N,N-dimethylethanamine (0.398 mol) and dissolving trimethoxysilane (0.398 mol), a commercially available platinum(0)-1,3-divinyl-1,1,3,3-tetramethyldisiloxane solution was added and the mixture was stirred for 24 hours under reflux. Upon completion of reaction, after removing the solvent through distillation under reduced pressure, 0.319 mol (yield: 80%) of the target compound was obtained by extracting with water and diethyl ether. $^1$H and $^{13}$C NMR spectroscopic data of the purified N,N-dimethyl-2-(3-(dimethoxymethylsilyl)propoxy)ethanamine are as follows.

$^1$H NMR (400 MHz, CDCl$_3$) δ 3.50 (8H, m), 3.39 (2H, t, J=6.4 Hz), 2.47 (2H, t, J=6.4 Hz), 2.24 (6H, s), 1.65 (2H, m), 0.60 (2H, t, J=8 Hz), 0.09 (3H, s); $^{13}$C NMR (100 MHz, CDCl$_3$) δ 73.6, 68.8, 58.9, 50.2, 45.9, 22.8, 9.1, −5.9.

Example 3

N,N-dimethyl-2-(3-(trimethoxysilyl)propoxy)propan-1-amine

Sodium hydride (17.5 g) and dimethyl formaldehyde (400 mL) were added to a 2-L round-bottom flask. After cooling the flask to 0° C. by immersing in an ice bath, 3-dimethylamino-1-propanol (0.398 mol) was added. After stirring for about 30 minutes and adding allyl bromide (0.4378 mol), the mixture was stirred for 3 hours after raising the temperature of the reactor to room temperature. Upon completion of reaction, the reaction was terminated by adding water to the flask and the product was extracted using diethyl ether. The extract was concentrated under reduced pressure and used in the next step without further purification. After filtration under reduced pressure, 3-(allyloxy)-N,N-dimethylpropan-1-amine was obtained through fractional distillation. Structural analysis was performed by NMR spectroscopy.

$^1$H NMR (400 MHz, CDCl$_3$) δ 5.91 (1H, m), 5.26 (1H, d, J=17.2 Hz), 5.15 (1H, d, J=17.2 Hz), 3.95 (2H, d, J=6.0 Hz), 3.45 (2H, t, J=6.0 Hz), 2.33 (2H, t, J=5.6 Hz), 2.20 (6H, s), 1.74 (2H, q, J=3.2 Hz); $^{13}$C NMR (100 MHz, CDCl$_3$) δ 135.0, 116.8, 71.8, 68.7, 56.7, 45.5, 28.0.

After adding toluene (200 mL) to a round-bottom flask containing 3-(allyloxy)-N,N-dimethylpropan-1-amine (0.398 mol) and dissolving trimethoxysilane (0.398 mol), a commercially available platinum(0)-1,3-divinyl-1,1,3,3-tetramethyldisiloxane solution was added and the mixture was stirred for 24 hours under reflux. Upon completion of reaction, after removing the solvent through distillation under reduced pressure, 0.340 mol (yield: 85%) of the target compound was obtained by extracting with water and diethyl ether. $^1$H and $^{13}$C NMR spectroscopic data of the purified N,N-dimethyl-2-(3-(trimethoxysilyl)propoxy)propan-1-amine are as follows.

$^1$H NMR (400 MHz, CDCl$_3$) δ 3.54 (9H, s), 3.36 (2H, t, J=6.4 Hz), 3.36 (2H, J=6.4 Hz), 2.31 (2H, t, J=6.4 Hz), 2.19 (6H, s), 1.72 (2H, m), 1.67 (2H, m), 0.64 (2H, t, J=8.0 Hz); $^{13}$C NMR (100 MHz, CDCl$_3$) δ 73.0, 69.0, 56.8, 50.5, 45.5, 28.0, 22.8, 5.3.

Example 4

N,N-dimethyl-2-(3-(dimethoxymethylsilyl)propoxy)propan-1-amine

Sodium hydride (17.5 g) and dimethyl formaldehyde (400 mL) were added to a 2-L round-bottom flask. After cooling the flask to 0° C. by immersing in an ice bath, 3-dimethylamino-1-propanol (0.398 mol) was added. After stirring for about 30 minutes and adding allyl bromide (0.4378 mol), the mixture was stirred for 3 hours after raising the temperature of the reactor to room temperature. Upon completion of reaction, the reaction was terminated by adding water to the flask and the product was extracted using diethyl ether. The extract was concentrated under reduced pressure and used in the next step without further purification. After filtration under reduced pressure, 3-(allyloxy)-N,N-dimethylpropan-1-amine was obtained through fractional distillation. Structural analysis was performed by NMR spectroscopy.

$^1$H NMR (400 MHz, CDCl$_3$) δ 5.91 (1H, m), 5.26 (1H, d, J=17.2 Hz), 5.15 (1H, d, J=17.2 Hz), 3.95 (2H, d, J=6.0 Hz), 3.45 (2H, t, J=6.0 Hz), 2.33 (2H, t, J=5.6 Hz), 2.20 (6H, s), 1.74 (2H, q, J=3.2 Hz); $^{13}$C NMR (100 MHz, CDCl$_3$) δ 135.0, 116.8, 71.8, 68.7, 56.7, 45.5, 28.0.

After adding toluene (200 mL) to a round-bottom flask containing 3-(allyloxy)-N,N-dimethylpropan-1-amine (0.398 mol) and dissolving trimethoxysilane (0.398 mol), a commercially available platinum(0)-1,3-divinyl-1,1,3,3-tetramethyldisiloxane solution was added and the mixture was stirred for 24 hours under reflux. Upon completion of reaction, after removing the solvent through distillation under reduced pressure, 0.339 mol (yield: 85%) of the target compound was obtained by extracting with water and diethyl ether. $^1$H and $^{13}$C NMR spectroscopic data of the purified N,N-dimethyl-2-(3-(dimethoxymethylsilyl)propoxy)propan-1-amine are as follows.

$^1$H NMR (400 MHz, CDCl$_3$) δ 3.29 (6H, s), 3.43 (2H, t, J=6.4 Hz), 3.35 (2H, J=6.4 Hz), 2.31 (2H, t, J=6.4 Hz), 2.20 (6H, s), 1.72 (2H, m), 1.62 (2H, m), 0.62 (2H, t, J=8.0 Hz), 0.09 (3H, s); $^{13}$C NMR (100 MHz, CDCl$_3$) δ 73.2, 69.1, 56.8, 50.2, 45.5, 28.0, 22.9, 9.1, −5.9.

Comparative Example 1

N,N-dimethylaminopropyltrimethoxysilane

N,N-Dimethylaminopropyltrimethoxysilane was purchased from Aldrich.

Comparative Example 2

N,N-bis(trimethylsilyl)aminopropyltrimethoxysilane

Aminopropyltrimethoxysilane (0.398 mol) and triethylamine (100 mL) were dissolved in dichloromethane (200 mL) in a round-bottom flask and trimethylsilyl chloride (0.800 mol) was added in a dropwise manner. After the addition was completed, the mixture was stirred at room temperature for 24 hours. Upon completion of reaction, N,N-bis(trimethylsilyl)aminopropyltrimethoxysilane (yield: 89%) was obtained through concentration under reduced pressure and fractional distillation. $^1$H and $^{13}$C NMR spectroscopic data of the purified N,N-bis(trimethylsilyl)aminopropyltrimethoxysilane are as follows.

$^1$H NMR (400 MHz, CDCl$_3$) δ 3.49 (9H, s), 2.70 (2H, t, J=6.4 Hz), 1.36 (2H, m), 0.47 (2H, t, J=6.4 Hz), 0.06 (18H, s); $^{13}$C NMR (100 MHz, CDCl$_3$) δ 50.1, 48.8, 28.3, 10.2, 2.06.

Test Example

1. Storage Stability Test

The storage stability of the alkylalkoxysilane compounds represented by Chemical Formula 1 according to the present invention was compared with the existing compounds.

The storage stability was tested by NMR spectroscopy. In order to obtain time-dependent spectrum, a CDCl₃ solution of the prepared alkoxysilane compound (0.1 M) was stored at room temperature and the integral of the peak of the alkoxy group bound to silicon was calculated by NMR with time. The degree of deformation of the compound was measured as percentage of the integral with respect to that at 0 hour. The result is given in Table 1.

TABLE 1

| Tested compounds | Storage stability (%) | | | | |
| --- | --- | --- | --- | --- | --- |
| | 0 hour | 1 day | 7 days | 30 days | 180 days |
| N,N-Dimethyl-2-(3-(trimethoxysilyl)propoxy)ethanamine (Example 1) | 100 | 99 | 99 | 97 | 81 |
| N,N-Dimethyl-2-(3-(dimethoxymethylsilyl)propoxy)ethanamine (Example 2) | 100 | 100 | 98 | 98 | 81 |
| N,N-Dimethyl-2-(3-(trimethoxysilyl)propoxy)propan-1-amine (Example 3) | 100 | 98 | 97 | 96 | 80 |
| N,N-Dimethyl-2-(3-(dimethoxymethylsilyl)propoxy)propan-1-amine (Example 4) | 100 | 99 | 99 | 98 | 79 |
| N,N-Dimethylaminopropyltrimethoxysilane (Comparative Example 1) | 100 | 97 | 80 | 72 | 51 |
| N,N-Bis(trimethylsilyl)aminopropyltrimethoxysilane (Comparative Example 2) | 100 | 90 | 76 | 65 | 42 |

As seen from Table 1, whereas the existing silane compounds of Comparative Examples 1 and 2 showed very low storage stability of 51% and 42% after having been stored at room temperature for 180 days, the alkylalkoxysilane compounds of the present invention exhibited superior storage stability of 79% or higher.

2. Hydrophilicity Test

The hydrophilicity of the alkylalkoxysilane compounds represented by Chemical Formula 1 according to the present invention was compared with the existing compounds.

The hydrophilicity was tested according to the method described in the literature [Zhang, X.; Kono, H.; Liu, Z.; Nishimoto, S.; Tryk, D. A.; Murakami, T.; Sakai, H.; Abe, M.; Fujishima, A. *Chem. Comm.* 2007, 4949-4951]. Specifically, a titanium oxide slurry was spin-coated on glass surface and heat-treated to obtain a titanium oxide-coated film. Then, the alkylalkoxy silane compound represented by Chemical Formula 1 or the existing compound was deposited on the film by chemical vapor deposition to obtain a TiO₂ film coated with the alkylalkoxysilane compound. Contact angle was measured to examine the hydrophilicity of the film. The contact angle was measured at room temperature using an automatic contact angle meter according to the sessile drop method. The result is given in Table 2.

TABLE 2

| Tested compounds | Contact angle |
| --- | --- |
| N,N-dimethyl-2-(3-(trimethoxysilyl)propoxy)ethanamine (Example 1) | 43° |
| N,N-dimethyl-2-(3-(dimethoxymethylsilyl)propoxy)ethanamine (Example 2) | 41° |
| N,N-dimethyl-2-(3-(trimethoxysilyl)propoxy)propan-1-amine (Example 3) | 42° |
| N,N-dimethyl-2-(3-(dimethoxymethylsilyl)propoxy)propan-1-amine (Example 4) | 40° |
| N,N-dimethylaminopropyltrimethoxysilane (Comparative Example 1) | 54° |
| N,N-bis(trimethylsilyl)aminopropyltrimethoxysilane (Comparative Example 2) | 53° |

As seen from Table 2, whereas the contact angle of the existing silane compounds of Comparative Examples 1 and 2 was 53° and 54°, the alkylalkoxysilane compounds according to the present invention showed relatively superior hydrophilicity with a contact angle ranging from 40° to 43°.

As demonstrated above, the alkylalkoxysilane compound represented by Chemical Formula 1 according to the present invention, which has an ether group and an dialkylamino group in an alkyl chain, has remarkably improved storage stability and hydrophilicity as compared to the existing silane compound having only a dialkylamino group.

The alkylalkoxysilane compound of the present invention, which has an ether group and an dialkylamino group in the alkyl chain, can provide hydrophilicity to a polymer when used as a polymer end modifier.

The alkylalkoxysilane compound of the present invention is capable of hydrogen bonding because the oxygen atom in the ether group has high electronegativity.

A polymer prepared using the alkylalkoxysilane compound of the present invention as a polymer modifier, a coupling agent, a surface treating agent, an adhesive, a coating agent, etc. has improved compatibility with adhesives and improved dispersibility owing to increased hydrophilicity.

The present invention has been described in detail with reference to specific embodiments thereof. However, it will be appreciated by those skilled in the art that various changes and modifications may be made in these embodiments without departing from the principles and spirit of the invention, the scope of which is defined in the appended claims and their equivalents.

What is claimed is:

1. A method for preparing an alkylalkoxysilane compound, comprising: preparing an intermediate compound of Chemical Formula 4 by coupling an allyl halide compound of Chemical Formula 2 with an N,N-dialkylaminoalkanol of Chemical Formula 3 in the presence of a base:

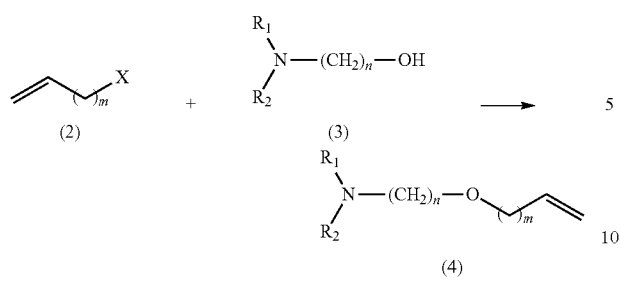

(2)        (3)

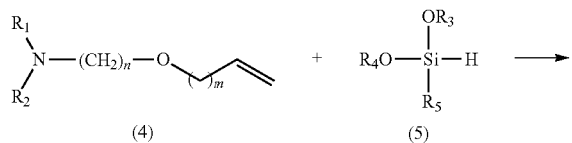

(4)

(wherein $R_1$ and $R_2$ is the same or different unsubstituted $C_1$-$C_{10}$ alkyl group; n is an integer from 0 to 5; and m is an integer from 0 to 3); and preparing an alkylalkoxysilane compound of Chemical Formula 1 by hydrosilylating the intermediate compound of Chemical Formula 4 with a silane compound of Chemical Formula 5:

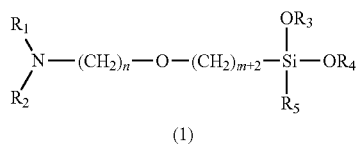

(4)        (5)

(1)

(wherein $R_1$, $R_2$, $R_3$ and $R_4$ is the same or different unsubstituted $C_1$-$C_{10}$ alkyl group; $R_5$ is an unsubstituted $C_1$-$C_{10}$ alkyl group or an unsubstituted $C_1$-$C_{10}$ alkoxy group; and n is an integer from 0 to 5; and m is an integer from 0 to 3).

2. The method for preparing an alkylalkoxysilane compound according to claim 1, wherein the coupling reaction is performed at −30° C. to 40° C. in the presence of sodium hydride or sodium hydroxide as a base.

3. The method for preparing an alkylalkoxysilane compound according to claim 1, wherein the hydrosilylation reaction is performed at 100° C. to 180° C. in the presence of a platinum (Pt) catalyst.

* * * * *